United States Patent [19]

Sérodes et al.

[11] Patent Number: 5,675,504
[45] Date of Patent: Oct. 7, 1997

[54] METHOD OF PREDICTING RESIDUAL CHLORINE IN WATER SUPPLY SYSTEMS

[75] Inventors: Jean Sérodes, Sillery; Manuel Rodriguez, Quebec, both of Canada

[73] Assignee: Universite Laval, Quebec, Canada

[21] Appl. No.: 589,869

[22] Filed: Jan. 23, 1996

[51] Int. Cl.$^6$ .................................................. G06F 15/18
[52] U.S. Cl. ................................................ 364/496; 395/911
[58] Field of Search ........................................ 364/496, 497, 364/499, 500, 550, 578; 395/914, 902, 903, 911, 21; 210/754, 739, 742

[56] References Cited

U.S. PATENT DOCUMENTS

| | | | |
|---|---|---|---|
| 4,435,291 | 3/1984 | Matsko | 210/739 |
| 4,997,574 | 3/1991 | Sarunac | 210/739 |
| 5,011,613 | 4/1991 | Feray et al. | 210/739 |
| 5,236,600 | 8/1993 | Hutchins | 210/739 |
| 5,446,829 | 8/1995 | Wang et al. | 395/24 |
| 5,581,459 | 12/1996 | Enbutsu et al. | 395/903 X |

OTHER PUBLICATIONS

Rossman et al. "Modeling Chlorine Residuals in Drinking–Water Distribution Systems" pp. 803–820.
Lawler et al. "Prediction of Total Residual Chlorine in Power Plant Discharges and Receiving Waters" Water Chlorination: Chemistry, Environmental Impact and Health Effects, Proceedings of the Fifth Conference 1986 pp. 1489–1501.

Primary Examiner—James P. Trammell
Assistant Examiner—M. Kemper
Attorney, Agent, or Firm—Foley & Lardner

[57] ABSTRACT

A method of configuring an artificial neural network for predicting residual chlorine concentration in water contained in a storage tank of a water supply system, the storage tank having an inlet for admitting water into the tank and an outlet for discharging water from the tank. The method of the invention comprises the steps of (a) collecting historical data representative of selected operational and water quality parameters associated with chlorine demand in the tank; (b) scaling the data collected in step (a); (c) organizing the data scaled in step (b) in the form of a set of time-lagged data; and (d) processing the data organized in step (c) through an artificial neural network by scanning a window over the set of data, the window having a size corresponding to a sub-set of the data, to associate a predicted value with a respective one of the sub-sets scanned by the window, the predicted value being representative of the residual chlorine concentration at the tank outlet. The artificial neural network is thus configured to recognize a set of data processed therethrough as corresponding substantially to one of the sub-sets of data and to associate with the recognized set of data the optimized predicted value associated with the sub-set of data.

22 Claims, 6 Drawing Sheets

METHOD OF PREDICTING RESIDUAL CHLORINE IN WATER SUPPLY SYSTEMS

BACKGROUND OF THE INVENTION

The present invention relates to improvements in the field of water treatment. More particularly, the invention is concerned with a method of predicting residual chlorine concentration in the water contained in a storage tank of a water supply system, at the tank outlet.

After being treated in a filtration plant, drinking water is disinfected in order to maintain sufficient disinfectant residual in the distribution system. The most commonly used disinfectant worldwide is chlorine ($Cl_2$). It is used as a post-disinfectant in an effort to ensure an acceptable microbiological water quality throughout the system and thus to protect consumers against waterborne diseases. When chlorine is injected in the treated water, it is gradually consumed by reaction with organic and inorganic compounds contained in the water and on pipeline walls. Apart from reacting with microbia, chlorine can also react with other compounds contained in the water, thereby forming the so-called disinfection-by-products (DBP) which are suspected to be carcinogenic. Accordingly, the quantities of chlorine added to water have to be minimized to prevent potential DBP formation, but adequate for ensuring a sufficient concentration of residual free chlorine instead of combined chlorine during distribution. Attaining this balance is a major challenge for treatment plant operators because of the continuous changes of water quality generally related with seasonal variations, which in turn require shifts in dosage quantities.

Chlorine is generally added at the final step of the treatment process (post-chlorination) and, if required, re-added within the distribution system (re-chlorination). After the injection of chlorine, water is stored in a tank whose role is to control the water flow demand and to ensure a sufficient contact time between the chlorine and the water. Operators can control the efficacy of chlorination by measuring the chlorine concentration at the outlet of the storage tank, in situ or using a monitor. This information is used to periodically adjust the chlorine dose levels. Although this practice is widespread, it is not precisely optimal because of the time delay associated with the residence time of water in the tank. That is, residual chlorine concentrations measured at the outlet of the tank at a specific time are not directly related to the doses of chlorine injected at the inlet of the tank. They are associated to past dose levels which obviously can no longer be adjusted. Therefore, the risk of underdose or overdose is always present and such a risk is particularly high in the periods of the year when water quality is constantly changing and chlorine demand is variable. Chlorine underdose means that chlorine is injected in insufficient amounts to prevent microbia re-growth, which represents an immediate potential public health problem, while chlorine overdose is related to aesthetic problems such as taste and odor as well as to an increase of DBP, a potential long term public health issue.

SUMMARY OF THE INVENTION

It is therefore an object of the invention to overcome the above drawbacks and to provide a method of predicting the residual chlorine concentration in water at the outlet of storage tanks of water supply systems.

Applicants have found quite unexpectedly that historical data representative of a number of parameters which are routinely measured in water treatment plants can be utilized to configure an artificial neural network (ANN) in a manner such as to predict the residual chlorine concentration at the tank outlet. An ANN is a tool capable of learning by means of representative data which characterize a given process; it is able to identify the intricacies of the process and to establish complex non-linear relationship between input and output variables. The present invention relies on the development of a method of configuring an ANN which allows the identification of chlorine evolution dynamics within a storage tank and, thus, the prediction of the residual chlorine concentration at the outlet of the tank.

According to one aspect of the invention, there is provided a method of configuring an ANN for predicting residual chlorine concentration in water contained in a storage tank of a water supply system, the storage tank having an inlet for admitting water into the tank and an outlet for discharging water from the tank. The method of the invention comprises the steps of:

a) collecting historical data representative of selected operational and water quality parameters associated with chlorine demand in the tank;

b) scaling the data collected in step (a);

c) organizing the data scaled in step (b) in the form of a set of time-lagged data;

d) processing the data organized in step (c) through an ANN having a plurality of nodes arranged to define an input layer, an output layer and at least one hidden layer therebetween, by scanning a window over the set of data, the window having a size corresponding to a sub-set of the data, to associate a predicted value with a respective one of the sub-sets scanned by the window, the predicted value being representative of the residual chlorine concentration at the tank outlet; and e) repeating step (d) while varying the size of the window and the number of nodes of the at least one hidden layer so as to optimize the predicted value; whereby the ANN is configured to recognize a set of data processed therethrough as corresponding substantially to one of the sub-sets of data and to associate with the recognized set of data the optimized predicted value associated with the sub-set of data.

The present invention also provides, in a second aspect thereof, a method of predicting residual chlorine concentration in water contained in a storage tank of a water supply system, which comprises the steps of:

a) collecting present and past data representative of selected operational and water quality parameters associated with chlorine demand in the tank;

b) scaling the data collected in step (a);

c) organizing the data scaled in step (b) in the form of a set of time-lagged data; and d) processing the data organized in step (c) through an ANN configured by a method as defined above, to provide at the output layer of the ANN a predicted value representative of the residual chlorine concentration at the tank outlet.

The historical data which is collected and processed through the ANN for the purpose of configuring same is representative of selected operational and water quality parameters which are associated with the chlorine demand in the storage tank. These selected parameters preferably include flowrate of water admitted into the tank, water temperature, chlorine concentration in water at the tank inlet, dose of chlorine injected in water and residual chlorine concentration in water at the tank outlet. The same parameters are selected when processing past and present data through the ANN for predicting the residual chlorine concentration at the tank outlet.

The frequency of data collecting corresponds to the frequency of water sampling or monitoring performed periodically at the water treatment plant and is in accordance with the mean residence time of water in the storage tank and with the desired prediction delay. In a preferred embodiment of the invention, data is collected at a frequency between one-fourth and one-half of the mean residence time. For example, if the mean residence time is about 4 days, data should be collected at a frequency between 1 and 2 days; in this case, if the desired delay in which the prediction is to be performed is 1 day, data should be obtained at a frequency of 1 day. Similarly, if the residence time is about 10 hours, data should be collected at a frequency between 2.5 and 5 hours; in this case, if the desired delay in which the prediction is to be performed is 3 hours, data should be obtained at a frequency of 3 hours. This allows for enough information to represent the dynamics of chlorine decay within the tank.

When sufficient information representing the variables described above is accumulated, the data is then scaled in order to build the desired ANN model. The method of the invention consists in training an ANN using information about the past conditions of these variables in order to determine future states of one of the variables, i.e. the residual chlorine concentration at the tank outlet. The training is accomplished by scanning a window over the data which contains the dynamics information about the variables described. Experimentation using different window sizes and ANN structures is carried out until the ANN model presenting the best prediction performance is achieved. At that time, the chosen ANN model is integrated into the routine management of a water supply system, to assist the operator in better accomplishing the chlorine dose adjustments. The ANN model is periodically upgraded when new data is available.

BRIEF DESCRIPTION OF THE DRAWINGS

Further features and advantages of the invention will become more readily apparent from the following description of preferred embodiments, reference being made to the accompanying drawings, in which FIG. 1 schematically illustrates a water treatment plant and water distribution system, both incorporating art ANN according to the invention, FIG. 2 schematically illustrates the structure of an ANN;

FIG. 2A illustrates a detail of FIG. 2;

DESCRIPTION OF PREFERRED EMBODIMENTS

Figure 1:
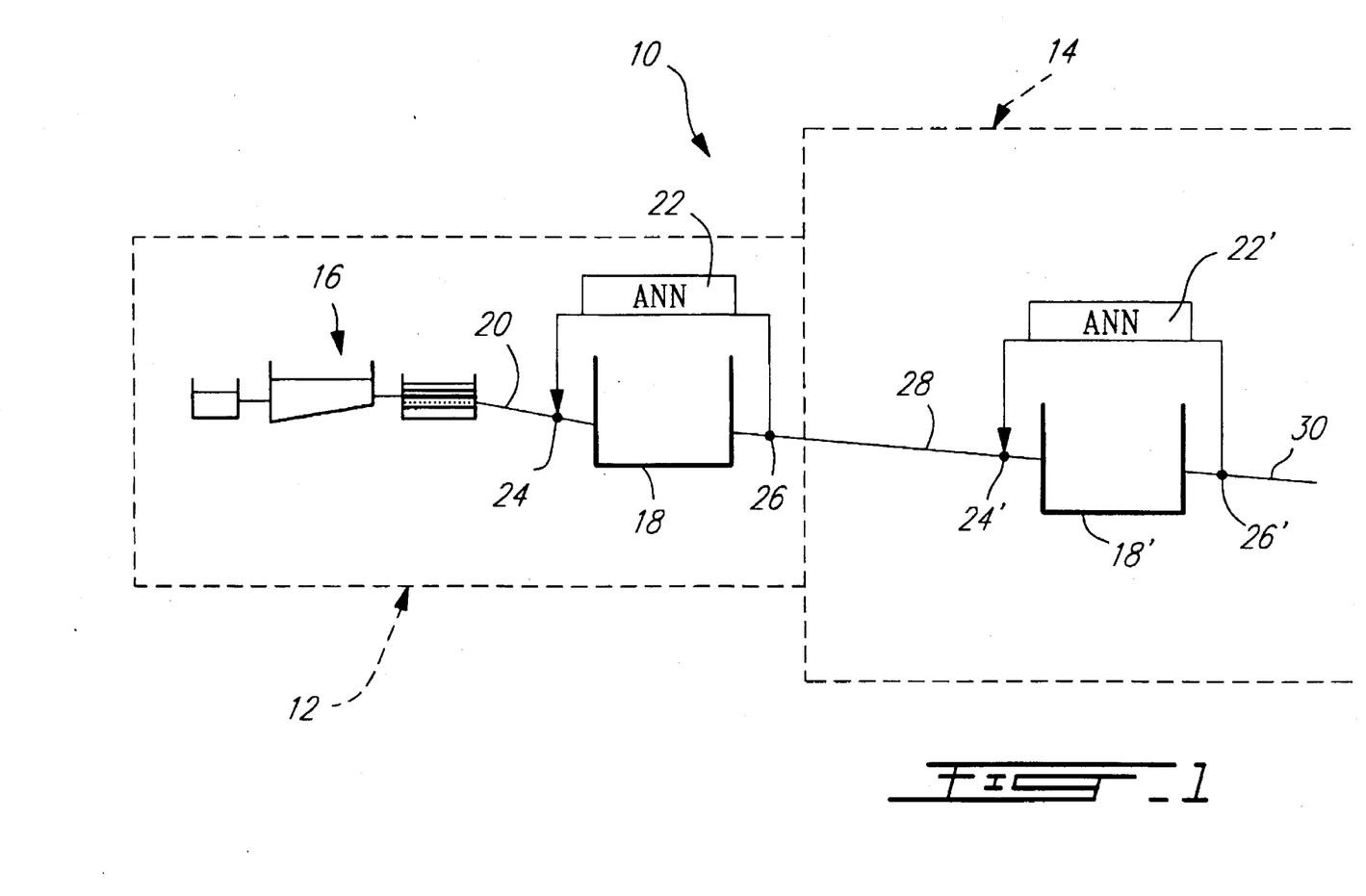

Referring first to FIG. 1, there is illustrated a water supply system which is generally designated by reference numeral 10 and includes a water treatment plant 12 and a water distribution system 14. The treatment plant 12 comprises a physical/chemical treatment unit 16 which is in fluid flow communication with a storage tank 18 via pipeline 20. An ANN 22 is associated with the tank 18. During post-chlorination, chlorine is injected at the inlet 24 of the tank; residual chlorine is monitored at the tank outlet 26. The treated and disinfected water discharged from the tank 18 is sent via pipeline 28 to the distribution system 14 which also comprises a storage tank 18' and an ANN 22'. If required, chlorine is re-added at the inlet 24' of the tank 22'. Residual chlorine is controlled at the tank outlet 26' prior to discharging the water throughout the system via pipeline 30.

The ANN's 22 and 22' serve to predict the residual chlorine concentration in the water at the tank outlets 26 and 26'. Information about residual chlorine concentration at the discharge of tank 18 or 18' constitutes valuable data for evaluation of the performance of the dose of chlorine injected at the tank inlet 24 or 24'. The ANN 22 or 22' provides this information in advance. According to the information, the operator is able to take the preventive measure of adjusting the required quantity of chlorine injected at the inlet 24 or 24' of tank 18 or 18'.

Figures 2, 2A:
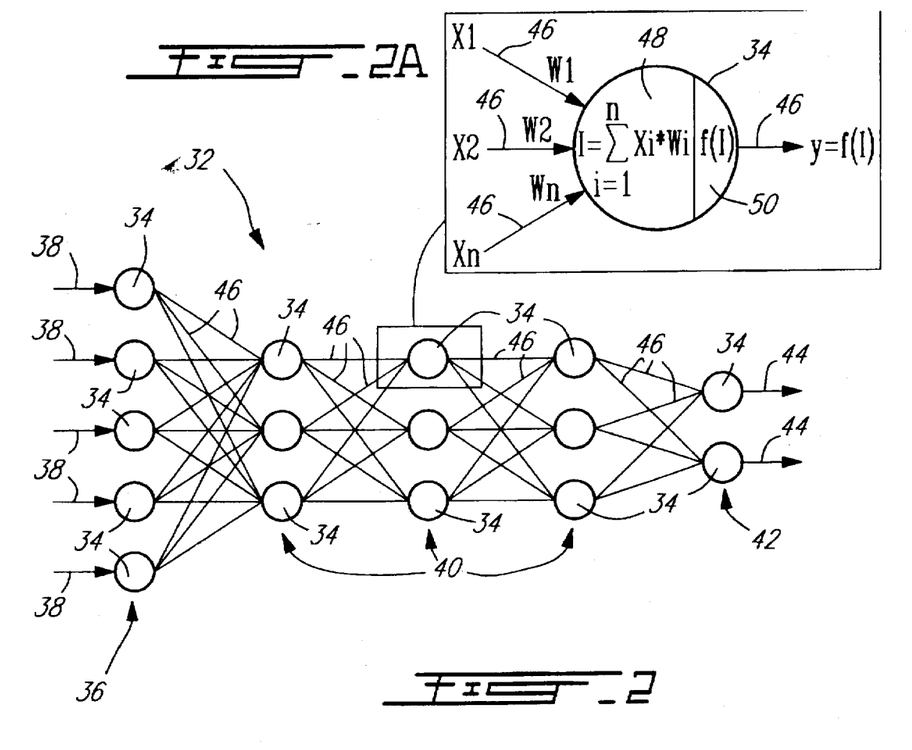

FIG. 2 illustrates the structure of a typical ANN 32. As shown, the ANN 32 comprises several layers of nodes 34: one input layer 36 that receives signal input vectors 38, one or more hidden layers 40 for processing information and one output layer 42 containing the response vectors 44 of the ANN. The nodes of a hidden layer are linked by connections 46 to nodes of the preceding or of the following layers. As shown in FIG. 2A, an individual node 34 may receive an input signal represented in the form of a vector $x_1, x_2, \ldots x_n$. The connections 16 are characterized by numeric weights $w_1, w_2, \ldots w_n$ and are responsible for activating each node 34. Inside each node, a summation function 48 converts the many input signals to a single signal I. A transfer function 50 processes the value of this signal. The final value y constitutes the output value of the node. This output may represent an input signal for nodes located further forward within the ANN.

Figure 3:
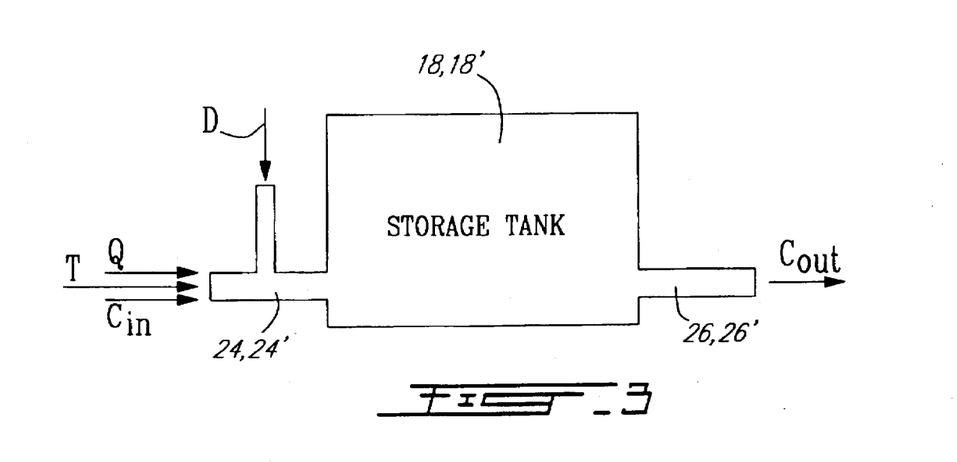
FIG. 3 schematically illustrates the storage tank used in the water treatment plant and water distribution system shown in FIG. 1.

FIG. 3 illustrates the part of the water supply system to be modeled, i.e. storage tank 18 or 18', and the parameters on which the model is based. The system being modeled is considered as a variable-volume reactor. Information about changes in flowrate Q of water admitted into the tank 18 or 18' in a continuous manner represents variations of operating pattern as well as the residence time of water within the tank. Information about the chlorine concentration $C_{in}$ at the inlet 24 or 24' (considered if residual chlorine is already present) and about the injected chlorine dose D represents the initial quantity of chlorine in the water entering the tank. $C_{in}$ is always taken into account if the tank is located within the distribution system 14; if the tank is located in the treatment plant 13, $C_{in}$ is taken into account only if pre-chlorination is applied during treatment and if all the chlorine is not consumed within the plant. Information about the temperature of water T represents the changes in kinetics governing the chlorine decay in the tank. Finally, residual chlorine $C_{out}$ at the tank outlet 26 or 26' represents the parameter to be predicted. Information about chlorine demand exerted by organic and inorganic compounds contained in water is intrinsically considered when temporal evolution of chlorine concentrations between the inlets 24,24' and outlets 26,26' is taken into account.

The development of the model is carried out using sufficient historical data representing all the variables described above, that is, a database comprising at least 400 observations of each of the variables. In the case of an hourly-based frequency of water sampling or monitoring, for example, this represents about 15 days of data; in the case of a daily-based frequency of water sampling or monitoring, this represents about 14 months of data. As previously indicated, data is collected at a frequency which corresponds to the frequency of water sampling or monitoring and is in accordance with the mean residence time of water in the tank and with the desired prediction delay.

The collected data has to be representative of the actual state of the treatment and distribution, that is, no changes in the operation characteristics of the plant should have been carried out within the period being considered (modification of basic water treatment, changes of chlorine injection point, changes in measurement methods, etc.). Moreover, a preliminary analysis of the data should be made in order to eliminate inconsistent observations which are related to analytical measurement errors, to uncalibrated monitors, to periods of chlorinator maintenance, etc.

Figure 4:
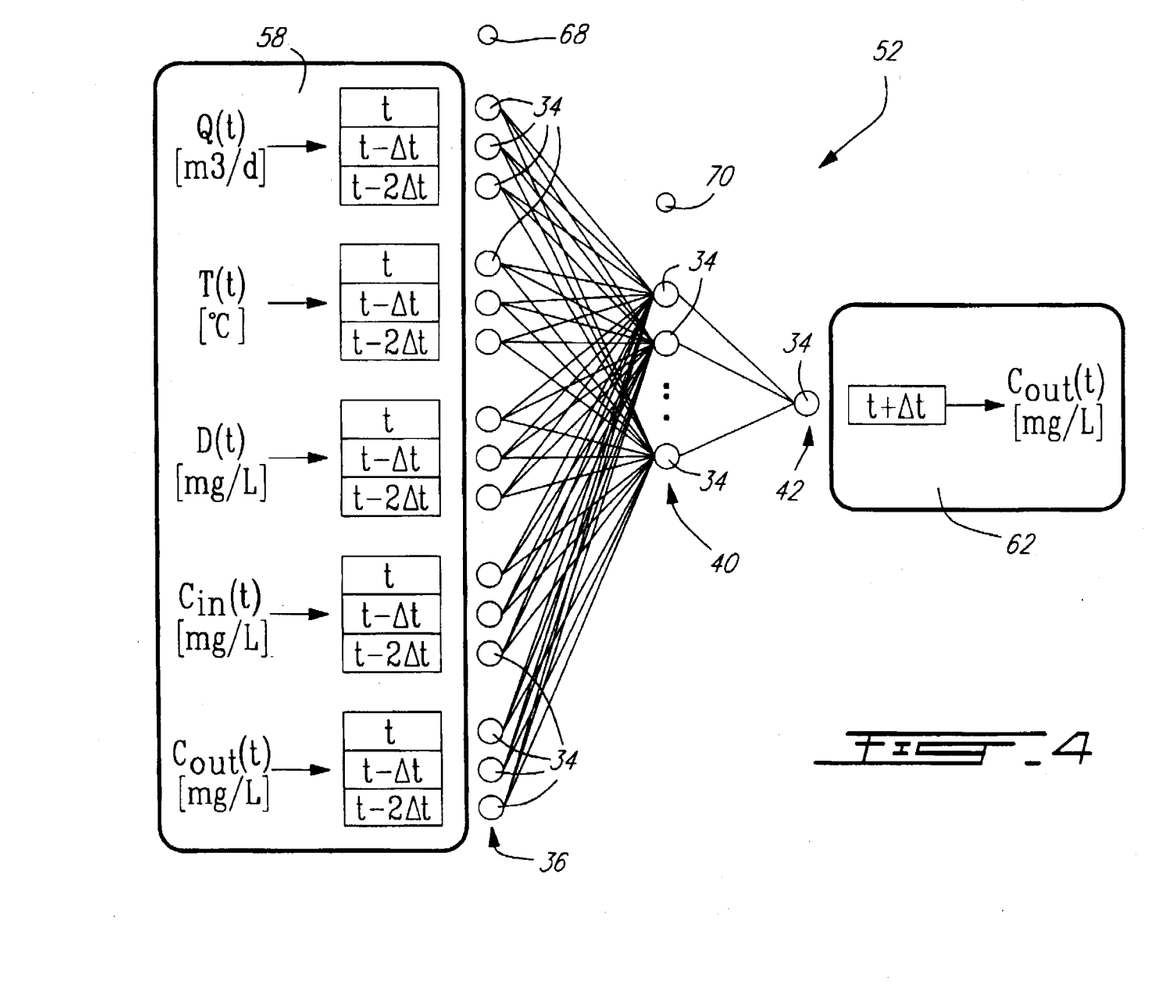
FIG. 4 schematically illustratres the structure of a three-layer ANN used in accordance with the invention.
Figure 5:
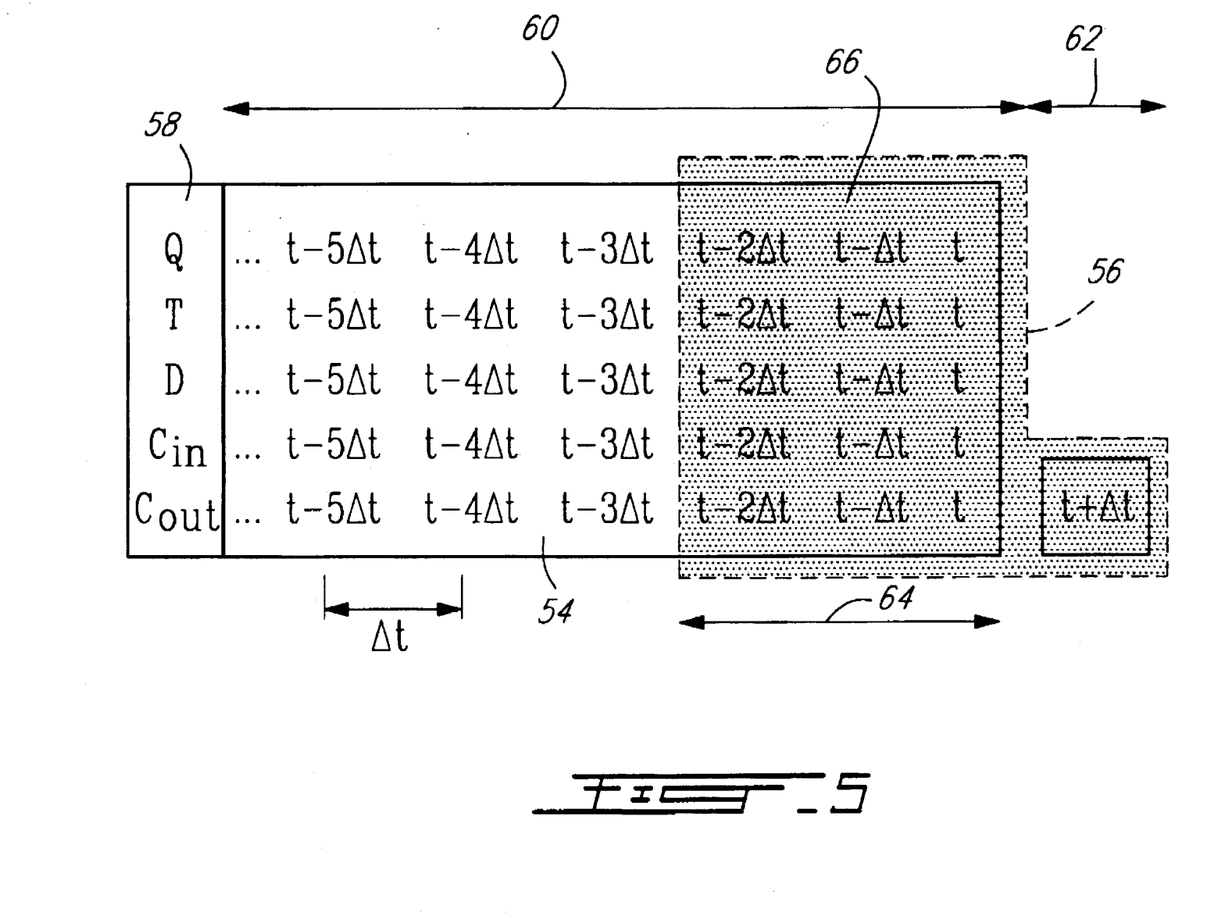
FIG. 5 schematically illustrates the window used for configuring the ANN shown in FIG. 4.

Once the collection stage is completed, the collected data is pre-processed and prepared to be taught to an ANN, preferably a three-layer ANN 52 as illustrated in FIG. 4. Thus, the collected data is first scaled linearly between 0 and 1 and then organized in the form of a set of time-lagged data 54 as shown in FIG. 5. Preferably, about 90% of the set of historical data is used for training the ANN 52 and about 10% of the set of historical data is used for evaluating same. At this point, the training process of the ANN begins.

As illustrated in FIG. 5, ANN training is accomplished by scanning a window 56 over the set of time-lagged data 54 which characterizes the parameters 58 associated with the chlorine demand in the storage tank 18 or 18'. Such a window represents a time-lagged scheme of the input and output variables 60,62 of the ANN. The input variables 60 represent the past information about the five parameters 58 described previously, including $C_{out}$, the residual chlorine concentration at the tank outlet, which is the parameter to predict. The output variable 62 represents information about the latter parameter $C_{out}$ to be predicted at a time delay $\Delta t$ relative to a selected time reference t. The time delay $\Delta t$ corresponds to the frequency of data collecting. For example, if the mean residence time of water in the tank is about 4 days and data is collected every day, $\Delta t$ is fixed at 1 day; if data is collected every 2 days, $\Delta t$ is fixed at 2 days. Similarly, if the mean residence time is about 10 hours and data is collected every 3 hours, $\Delta t$ is equal to 3 hours; if data is collected every 5 hours, $\Delta t$ is equal to 5 hours.

At the beginning of the training process, one size of window is chosen. The window size 64 is selected so that the window 56 initially scans a sub-set of input data 66 having a predetermined number of time intervals corresponding to the mean residence time of water in the tank. For example, if the mean residence time is about 3 days, a three-day lagged window is first selected, such as the window 56 shown in FIG. 5 where $\Delta t$ would be equal to 1 day. The training process using such a window then begins. As illustrated in FIG. 4, the number of nodes 24 of the input layer 36 is conditioned by the size of this window. This number is equal to the number of parameters 58 being considered, multiplied by the number of time intervals in the sub-set of data scanned by the window. For example, if a window scanning a sub-set of data having 3 time intervals (i.e. t−2$\Delta t$, t−1$\Delta t$ and t−0$\Delta t$) is used and the number of parameters is 5, the number of input nodes is equal to 15. Similarly, if a window scanning a sub-set of data having 5 time intervals (i.e., from t−4$\Delta t$ to 5−0$\Delta t$) is used and the number of parameters is 5, the number of input nodes is equal to 25. The output layer 42 comprises a single node 34 since there is only one predicted parameter, that is, $C_{out}$ at t+$\Delta t$. The number of nodes 34 in the hidden layer 40 is determined experimentally as will be explained hereinbelow. Nodes 68 and 70 represent the bias included in the input layer 36 and hidden layer 40, whose values are initially set to equal 1.

Figure 6:
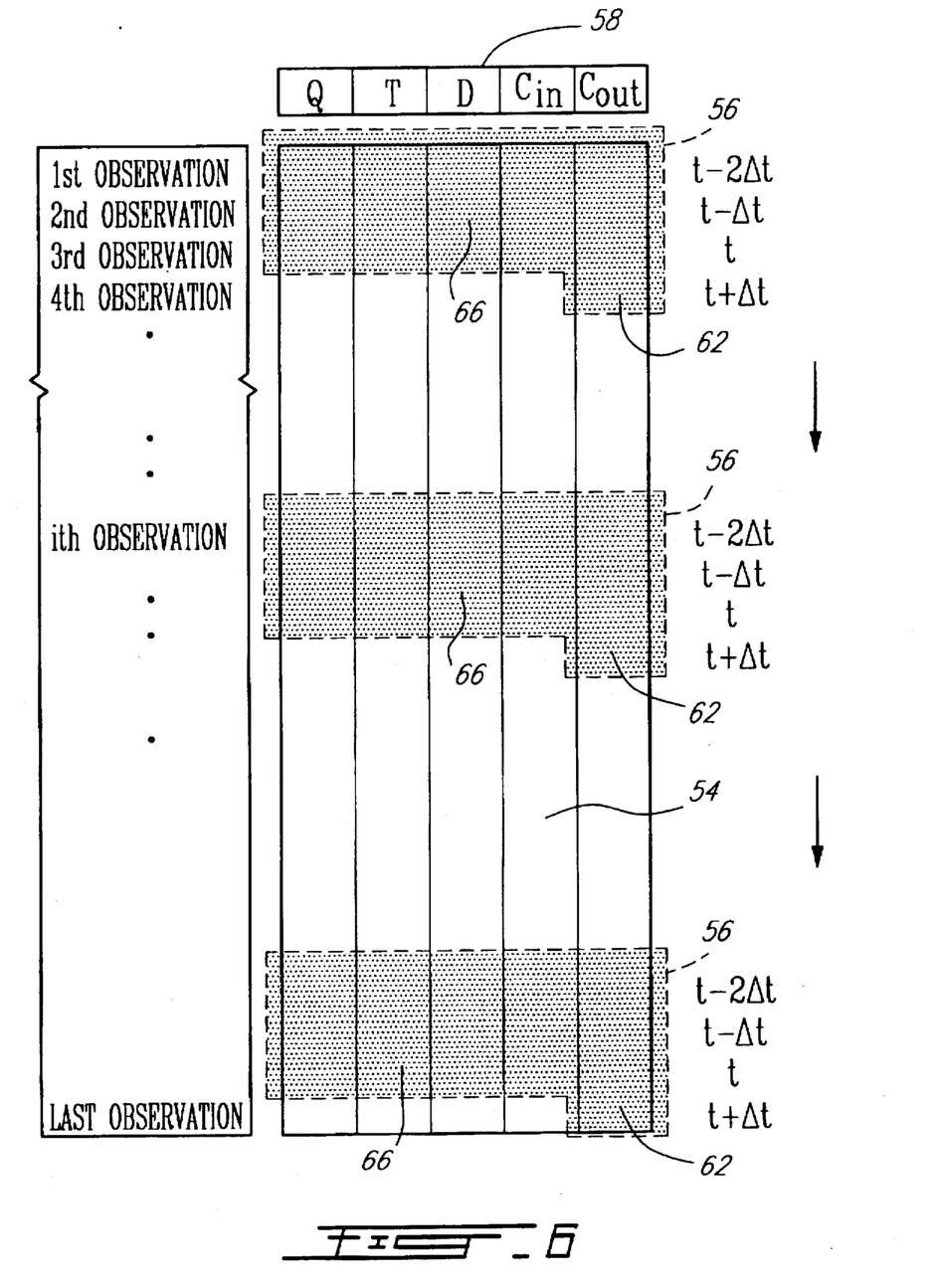
FIG. 6 illustrates the progress of the window shown in FIG. 5 throughout the database.

Before beginning the ANN training process, the number of nodes 34 in the hidden layer 40 is selected; to begin with, the same number of input nodes is chosen. As illustrated in FIG. 6, training consists in presenting the window 56 to the ANN at different positions over the database 54, from the beginning to the end. The training begins with the windows 56 placed at the beginning of the database 54. After a first sub-set of input-output data 66,62 is presented to the ANN, the window moves $\Delta t$ down the database and a second sub-set of data is presented. This process continues throughout the database so that the ANN is trained to associate a predicted output value 62 with a respective one of the sub-sets of input data 66 scanned by the window 56, the predicted output value 62 being representative of $C_{out}$ at t+$\Delta t$. When the window 56 reaches the end of the database 54, it is placed again at the beginning and the process is repeated. Each position of the window 56 over the database 54 corresponds to one sub-set of input-output data processed through the ANN and thus corresponds to one iteration. After each iteration, the ANN adjusts its connection weights according to a backpropagation algorithm until a root mean squared error (RMSE) equal to or less than 0.15 is obtained between a desired predicted value and the predicted value 62 provided at the output layer 42 (see FIG. 4). Use is preferably made of a backpropagation algorithm which is based on a gradient-descent delta rule and has a constant learning rate of 0.3 and a constant momentum of 0.9. Examples of commercially available software providing a backpropagation algorithm for ANN are Propagator™ from ARD Corp. (Maryland), NeuralWorks Explorer™ and NeuralWorks Professional™ from NeuralWare Inc. (Pennsylvania), Brain Maker Professional™ from California Scientific Software (California), Neuralyst™ from Epic Systems Corp. (California), Thinks™ from Logical Design Consulting (California), NeuralCASE™ from NeuroSym Corp. (Texas) and NueX™ from Charles River Analytics (Massachusetts). Generally, the number of iterations required to minimize the error between the desired predicted value and the output value 62 is equal to approximately 70 times the number of observations in the database; in other words, the window 54 passes 70 times throughout the entire database 56.

Figure 7:
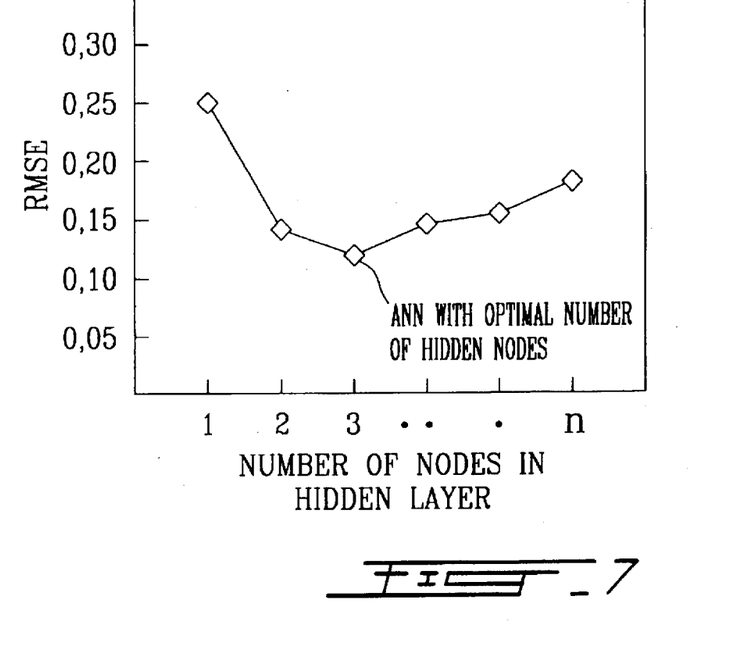
FIG. 7 is a plot of the root mean squared error against the number of nodes in the hidden layer of the ANN.

The same process described above is then carried out with the same window size, but varying the number of nodes 34 in the hidden layer 40, that is, by removing one node at the time. The smallest hidden layer is one which contains a single node. Each ANN developed as a result of using a different number of nodes in the hidden layer is evaluated by means of the RMSE as a performance criteria. Results of ANN are considered acceptable only if the RMSE is equal to or less than 0.15. When the results are deemed acceptable, the ANN configuration with the number of hidden nodes that gives the smallest RMSE is selected for the given window size, using a plot as illustrated in FIG. 7.

Figure 8:
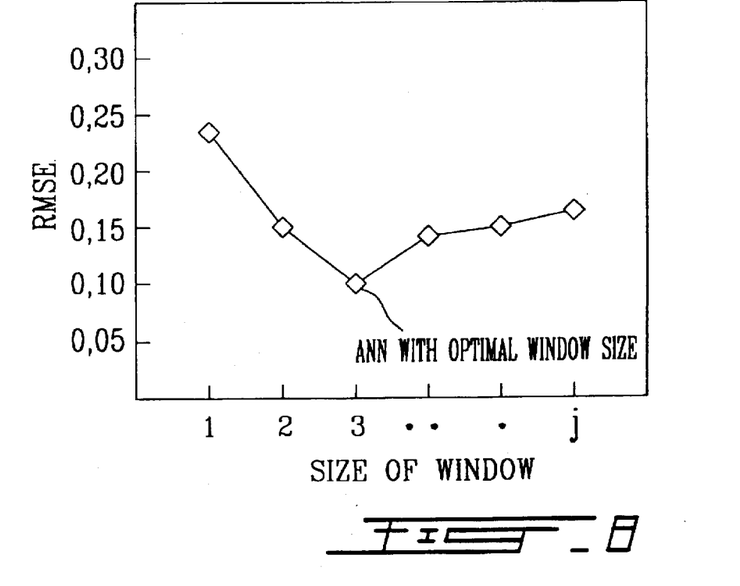
FIG. 8 is a plot of the root mean squared error against the size of the window.

Next, the process is repeated using a different window size, that is, using larger or smaller sizes. The smallest window size is one for which information corresponds solely to one time interval, that is, t−0$\Delta t$ (which is equal to t). The largest window tested is one for which the time-lagged data in the past is closest to (without exceeding) twice the mean residence time of water in the tank. For example, if the mean residence time is about 10 hours and Δt is equal to 3 hours, the largest window tested is one for which the time-lagged data in the past does not exceed 20 hours; in this case, 7 window sizes ranging from t−6Δt to t−0Δt (because 6Δt=18 hours, which is close to, but still less than, 20 hours) should be tested. The ANN configuration with the window size that gives the smallest RMSE is finally selected, using a plot as illustrated in FIG. 8.

Once the final ANN is chosen, it is integrated into the routine management of the water supply system 10 illustrated in FIG. 1. The ANN's 22,22' shown in FIG. 1 are thus configured to recognize a set of past and present data processed therethrough as corresponding substantially to one of the aforementioned sub-sets of data 66 and to associate with the recognized set of data the optimized predicted value 62 associated with the sub-set of data, such a value being the output value of each ANN and being representative of $C_{out}$ at t+Δt where t is present time. The predicted values of $C_{out}$ are used by operators as key information for correctly adjusting chlorine dosage.

The following Tables 1-4 illustrate the use of an ANN configured to predict at one day in the future (Δt=1 day) the residual chlorine concentration at the outlet of a storage tank within the water supply system of the city of Sainte-Foy, Quebec, Canada. In these examples, a three-day lagged window was selected.

TABLE 1

| | Q (m³/d) | T (°C.) | D (mg/L) | $C_{in}$ (mg/L) | $C_{out}$ (mg/L) |
|---|---|---|---|---|---|
| t − 2Δt (February 28th) | 12830 | 0.2 | 0.56 | 0.48 | 0.80 |
| t − Δt (March 1st) | 12290 | 0.2 | 0.49 | 0.49 | 0.74 |
| t (March 2nd) | 11490 | 0.3 | 0.40 | 0.73 | 0.10 |
| t + Δt (March 3rd) | | | | Measured | 0.63 |
| | | | | ANN prediction | 0.61 |

TABLE 2

| | Q (m³/d) | T (°C.) | D (mg/L) | $C_{in}$ (mg/L) | $C_{out}$ (mg/L) |
|---|---|---|---|---|---|
| t − 2Δt (March 5th) | 10290 | 0.2 | 0.39 | 0.81 | 0.61 |
| t − 2Δt (March 6th) | 10980 | 0.2 | 0.54 | 0.81 | 0.66 |
| t (March 7th) | 10710 | 0.3 | 0.61 | 0.72 | 0.72 |
| t + Δt (March 8th) | | | | Measured | 0.73 |
| | | | | ANN prediction | 0.74 |

TABLE 3

| | Q (m³/d) | T (°C.) | D (mg/L) | $C_{in}$ (mg/L) | $C_{out}$ (mg/L) |
|---|---|---|---|---|---|
| t − 2Δt (July 4th) | 11570 | 20 | 1.29 | 0.64 | 0.64 |
| t − Δt (July 5th) | 7950 | 20 | 1.45 | 0.87 | 0.50 |
| t (July 6th) | 8250 | 20 | 1.65 | 0.79 | 0.67 |
| t + Δt (July 7th) | | | | Measured | 0.84 |
| | | | | ANN prediction | 0.87 |

TABLE 4

| | Q (m³/d) | T (°C.) | D (mg/L) | $C_{in}$ (mg/L) | $C_{out}$ (mg/L) |
|---|---|---|---|---|---|
| t − 2Δt (July 30th) | 11760 | 21 | 0.86 | 0.83 | 1.12 |
| t − Δt (July 31st) | 10900 | 21 | 0.80 | 0.84 | 1.13 |

TABLE 4-continued

| | Q (m³/d) | T (°C.) | D (mg/L) | $C_{in}$ (mg/L) | $C_{out}$ (mg/L) |
|---|---|---|---|---|---|
| t (Agusut 1st) | 13149 | 21 | 0.85 | 0.81 | 1.05 |
| t + Δt (August 2nd) | | | | Measured | 0.95 |
| | | | | ANN prediction | 0.97 |

As new data from routine management becomes available, the ANN is re-trained periodically and thus the model is continuously upgraded.

We claim:

1. A method of configuring an artificial neural network for predicting residual chlorine concentration in water contained in a storage tank of a water supply system, said storage tank having an inlet for admitting water into the tank and an outlet for discharging water from the tank, said method comprising the steps of:

a) collecting historical data representative of selected operational and water quality parameters associated with chlorine demand in said tank;

b) scaling the data collected in step (a);

c) organizing the data scaled in step (b) in the form of a set of time-lagged data;

d) processing the data organized in step (c) through an artificial neural network having a plurality of nodes arranged to define an input layer, an output layer and at least one hidden layer therebetween, by scanning a window over said set of data, said window having a size corresponding to a sub-set of said data, to associate a predicted value with a respective one of the sub-sets scanned by said window, said predicted value being representative of the residual chlorine concentration at the tank outlet; and e) repeating step (d) while varying the size of said window and the number of nodes of said at least one hidden layer so as to optimize said predicted value;

whereby said artificial neural network is configured to recognize a set of data processed therethrough as corresponding substantially to one of said sub-sets of data and to associate with the recognized set of data the optimized predicted value associated with said one sub-set of data.

2. A method as claimed in claim 1, wherein said selected operational and water quality parameters include flowrate of water admitted into said tank, water temperature, chlorine concentration in water at the tank inlet, dose of chlorine injected in water and residual chlorine concentration in water at the tank outlet, and wherein the water has a predetermined mean residence time in said tank.

3. A method as claimed in claim 2, wherein the historical data is collected in step (a) at a frequency ranging from one-fourth to one-half of said mean residence time.

4. A method as claimed in claim 3, wherein said predicted value is determined at a time delay relative to a selected time reference, said time delay corresponding to the frequency of data collecting.

5. A method as claimed in claim 1, wherein the collected data is scaled in step (b) linearly between 0 and 1.

6. A method as claimed in claim 1, wherein said artificial neural network comprises one hidden layer of nodes.

7. A method as claimed in claim 2, wherein said window has a size such as to initially scan a sub-set of data having a predetermined number of time intervals corresponding to said mean residence time and wherein the window size is thereafter varied in step (e).

8. A method as claimed in claim 7, wherein the input layer of said artificial neural network has a number of nodes at least equal to the number of said parameters multiplied by said predetermined number of time intervals.

9. A method as claimed in claim 8, wherein said artificial neural network comprises one hidden layer having a number of nodes ranging from 1 to the number of nodes of said input layer.

10. A method as claimed in claim 1, wherein said artificial neural network includes a plurality of connection weights each associated with a respective one of said nodes of said at least one hidden layer, and wherein step (d) is repeated in step (e) a number of times using the same set of historical data while adjusting said connection weights according to a backpropagation algorithm until a root mean squarred error equal to or less than 0.15 is obtained between a desired predicted value and the predicted value provided at said output layer.

11. A method as claimed in claim 10, wherein said backpropagation algorithm is based on a gradient-descent delta rule and has a constant learning rate of 0.3 and a constant momentum of 0.9.

12. A method as claimed in claim 10, wherein the number of times that step (d) is repeated is about 70.

13. A method as claimed in claim 10, wherein the number of nodes of said at least one hidden layer is varied in step (e) until the smallest root mean squarred error is obtained.

14. A method as claimed in claim 10, wherein the size of said window is varied in step (e) until the smallest root mean squared error is obtained.

15. A method as claimed in claim 10, wherein about 90% of said set of historical data is used for training said artificial neural network and about 10% of said set of historical data is used for evaluating same.

16. A method of predicting residual chlorine concentration in water contained in a storage tank of a water supply system, said storage tank having an inlet for admitting water into the tank and an outlet for discharging water from the tank, said method comprising the steps of:

a) collecting present and past data representative of selected operational and water quality parameters associated with chlorine demand in said tank;

b) scaling the data collected in step (a);

c) organizing the data scaled in step (b) in the form of a set of time-lagged data; and d) processing the data organized in step (c) through an artificial neural network configured by a method as defined in claim 1, to provide at the output layer of said network a predicted value representative of the residual chlorine concentration at the tank outlet.

17. A method as claimed in claim 16, wherein said selected operational and water quality parameters include flowrate of water admitted into said tank, water temperature, chlorine concentration in water at the tank inlet, dose of chlorine injected in water and residual chlorine concentration in water at the tank outlet, and wherein the water has a predetermined mean residence time in said tank.

18. A method as claimed in claim 17, wherein the present and past data are collected in step (a) at a frequency ranging from one-fourth to one-half of said mean residence time.

19. A method as claimed in claim 18, wherein prediction of the residual chlorine at the tank outlet is performed at a time delay relative to present time, said time delay corresponding to the frequency of data collecting.

20. A method as claimed in claim 18, wherein the collected data is scaled in step (b) linearly between 0 and 1.

21. A method as claimed in claim 16, wherein said storage tank is located downstream of a post-chlorination station.

22. A method as claimed in claim 16, wherein said storage tank is located downstream of a re-chlorination station.

* * * * *